United States Patent [19]
Wallace et al.

[11] Patent Number: 5,984,879
[45] Date of Patent: Nov. 16, 1999

[54] INTRAUTERINE PRESSURE CATHETER DEVICE

[75] Inventors: W. Dean Wallace, Salt Lake City; Christopher A. Cutler, Centerville; Steven R. Smith, Draper, all of Utah

[73] Assignee: Clinical Innovation Associates, Inc., Murray, Utah

[21] Appl. No.: 08/706,837

[22] Filed: Sep. 3, 1996

[51] Int. Cl.[6] .............................. A61B 5/103; A61B 5/117
[52] U.S. Cl. ........................... 600/587; 600/591; 600/585
[58] Field of Search ...................... 128/778, 748, 128/775, 698, 774, 733, 675; 606/192, 194, 195, 198; 600/587, 588, 561, 591, 593, 585, 376

[56] References Cited

U.S. PATENT DOCUMENTS

| | | | |
|---|---|---|---|
| 4,519,401 | 5/1985 | Ko et al. | 73/721 |
| 4,722,730 | 2/1988 | Levy et al. | 128/775 |
| 4,785,822 | 11/1988 | Wallace . | |
| 4,966,161 | 10/1990 | Wallace et al. | 128/778 |
| 5,154,179 | 10/1992 | Ratner | 604/264 |
| 5,218,972 | 6/1993 | Gorsuch et al. | 128/775 |
| 5,279,308 | 1/1994 | DiSabito et al. | 128/775 |
| 5,286,259 | 2/1994 | Ganguly et al. | 606/194 |
| 5,425,362 | 6/1995 | Siker et al. | 600/549 |
| 5,427,114 | 6/1995 | Colliver et al. | 128/748 |
| 5,433,216 | 7/1995 | Sugrue et al. | 128/778 |
| 5,566,680 | 10/1996 | Urion et al. | 128/775 |
| 5,573,007 | 11/1996 | Bobo, Sr. | 128/748 |

OTHER PUBLICATIONS

Life Trace™ brochure regarding Intrauterine Pressure Catheters, 1995.
Corometrics Medical Systems, Inc. brochure regarding Intrauterine Catheter Tip Transducer, undated.
Utah Medical Products, Inc. brochure regarding Intrauterine Pressure Catheter System—Intran™ Plus IUP–400, 1990.
Utah Medical Products, Inc. brochure regarding IUP catheters, 1992.
Brochure regarding Transducer—tipped IUP catheters, undated.

Primary Examiner—Richard J. Apley
Assistant Examiner—Justine R. Yu
Attorney, Agent, or Firm—Trask, Britt & Rossa

[57] ABSTRACT

A pressure catheter for monitoring changes in pressure within the body is comprised of an outer hollow tube containing a fluid channel and a closed air column having a pressure-compliant member which is deformable upon an increase in pressure. A change in pressure deforms the pressure-compliant member, which modifies the pressure in the air column, and is translated to a pressure sensor which converts the pressure change data to an electrical signal recognizable by a fetal monitor. The pressure catheter of the present invention is particularly suitable for intrauterine pressure monitoring during labor.

17 Claims, 5 Drawing Sheets

INTRAUTERINE PRESSURE CATHETER DEVICE

BACKGROUND

Field of the Invention: This invention relates to devices for detecting changes in intrauterine pressure during labor, and specifically relates to catheter devices for determining pressure changes in the uterus through transference of uterine pressure to a gas-containing compliant chamber associated with a closed air column.

Statement of the Art: It has become common practice in the delivery and birth of a baby to monitor intrauterine conditions throughout the period of labor. Monitoring the intrauterine environment, including fetal heart rate and uterine contractions, enables the attending medical personnel to evaluate the progress of the delivery and to diagnose the existence of, or potential for, emergency situations which require immediate attention or action. Where intrauterine monitoring was once of singular importance in high risk and difficult deliveries, it has now become a routine part of the delivery procedure in many births. While only ten percent of all births are considered to be high-risk, warranting the use of intrauterine monitoring, intrauterine monitoring is used in sixty to seventy percent of all births regardless of the level of risk attributed to the birth. In actuality, about twenty percent of births experience complications.

It has long been recognized that an important relationship exists between fetal heart rate (FHR) and intrauterine pressure (IUP) and that such data relates to the well-being of the fetus during labor and delivery. Historically, two types of uterine monitoring have been practiced—external and internal. External uterine monitoring essentially comprises the attachment of a monitoring device to the mother's abdomen. The external uterine monitoring device generally detects fetal heart rate, and may have some capability for detecting intrauterine pressure or other indicia of the labor process. However, external monitoring is limited in its effectiveness because of the inaccuracy of readings obtained from the device. As uterine contractions increase, more "noise" is detected in such systems and data output becomes difficult to interpret. In addition, externally attached uterine monitoring devices move when the patient moves and, therefore, require frequent repositioning.

Known internal uterine monitoring systems, or "intrauterine" devices, include fetal scalp electrodes and pressure sensors positioned within the uterus. Internal monitoring systems are more accurate than external monitoring devices because they detect intrauterine conditions directly and thereby avoid the inaccuracy introduced by noise and other detection artifacts experienced with external uterine monitoring devices.

A number of intrauterine monitoring devices have been disclosed in the patent literature, including U.S. Pat. No. 4,785,822 to Wallace; U.S. Pat. No. 4,966,161 to Wallace, et al.; and U.S. Pat. No. 5,279,308 to DiSabito, et al. Those and other intrauterine pressure monitors employ one of two basic types of pressure detection. One type of pressure detection employs a fluid-filled tube which translates a mechanical change in fluid level within the tube to an electrical signal. A second type of pressure detection employs an electronic sensor positioned near the distal end of the device inserted in the uterus. Both types of intrauterine pressure detection devices detect timing and magnitude of changes in pressure within the uterus. Such changes within the uterus are indicative of phases of uterine contraction, and relate to the well-being and status of the fetus during labor and delivery.

While intrauterine monitoring devices are more preferred than external uterine monitoring devices for the reasons given above, the performance of fluid-filled IUP devices can be problematic because the tubing of such devices can become clogged with particulate matter from the uterus or amniotic fluid. As a result, flushing and recalibration of fluid-filled IUP devices are frequently necessary. While flushing and recalibration are not difficult in such devices, the sterility of the device may be severely compromised and interruption of the monitoring procedure is inconvenient. In addition, fluid-filled IUP devices require refilling and recalibration if the patient is ambulatory. Therefore, use of such fluid-filled IUP devices may limit the ability of the patient to move or walk around during long periods of labor.

Recognizing the drawbacks and inherent problems associated with fluid-filled IUP devices, others have developed gas column pressure catheters for use in monitoring pressures in vessels and cavities of the human body. A catheter of such type is disclosed in U.S. Pat. No. 5,573,007 to Bobo. Gas column devices of the type disclosed in the pending application to Bobo are suitable for use in vessels or cavities where little or no impact may be encountered by the gas-filled chamber of the device. However, in applications where the gas-filled chamber is likely to encounter movement (e.g., the movement of a fetus in utero) or be crushed by other means such as bending of an artery or vein as the patient moves, the gas-filled chamber is crushed or deflated and proper pressure monitoring cannot be conducted. That problem has been addressed in some designs by providing dual gas-filled chambers for pressure monitoring so that if one is crushed or otherwise rendered inoperable because of surrounding conditions, presumably the other gas-filled chamber will operate.

Sensor-tipped IUP devices are the more recently developed of the IUP devices and have gained great popularity over fluid-filled devices because of the relative convenience in use. Minimal setup procedures are required with the sensor-tipped devices other than "zeroing" the device. Zeroing the device involves setting the base pressure to match that of the atmosphere while no pressure is being applied to the catheter. Once inserted, the catheter is connected to a fetal monitor using a reusable interface cable in the same way that the remote sensor of a fluid-filled catheter is connected to a fetal monitor.

Despite the advantages that sensor-tipped IUP devices present over fluid-filled IUP devices, known sensor-tipped devices still have certain disadvantages in use. For example, known sensor-tipped IUP devices have an enlarged tip to accommodate the sensor located in the tip, and the enlarged tip often causes discomfort during insertion. Discomfort is also caused by the hardness of the material used to manufacture the tip. The major disadvantage of inserting sensor-tipped IUP devices, as well as fluid-filled IUP devices, is the possibility of perforating the placenta or uterus as a result of the higher insertion force required to insert the larger tip. More incidences of perforation are experienced with sensor-tipped IUP devices, and deaths have been reported of both fetuses and mothers from damage caused by insertion of sensor-tipped devices. A sensation of tingling at the site of the sensor has also been reported by some patients due to the electrical current which runs through the IUP device to the sensor in the tip.

Thus, it would be advantageous to the field of obstetrics to provide an intrauterine pressure monitor which is simple in construction, which is easily and quickly calibrated for accurately monitoring pressure changes, which is structured for easy and safe insertion into the uterus, which is structured to avoid damaging the uterus or endangering the fetus, which minimizes discomfort to the patient and which permits the patient to move freely without compromising the calibration or operation of the device.

SUMMARY OF THE INVENTION

In accordance with the present invention, a disposable pressure catheter device is structured with a closed air column coupled to a pressure detection device, the air column having a pressure-compliant member which is deformable upon a change in pressure experienced within a body to translate such change in pressure through the air column to the pressure detection means. The pressure catheter device of the present invention can be adapted for use in a variety of medical procedures where changes in pressure within the body are to be detected, such as arterial pressure monitoring, cardiac pressure monitoring, pulmonary artery pressure monitoring and intracranial monitoring. However, the present invention is particularly suited for use in intrauterine pressure detection during labor and will be described herein with respect to that exemplar application.

The intrauterine pressure catheter device of the present invention is generally comprised of a catheter having an elongated outer hollow tube in which is disposed a substantially co-extensive inner tube defining an internal air column. At the proximal end of the catheter is a housing to which the outer hollow tube and inner tube are attached. The housing provides a means of connecting the catheter to a reusable interface cable, or connector, which is in turn connected to a fetal monitor unit. As used herein, "proximal" refers to that end of the pressure catheter device which is positioned outside the uterus and away from the patient's body, and "distal" refers to that end of the pressure catheter device which is positioned within or toward the uterus of the patient.

The outer hollow tube of the catheter is made from a biocompatible and flexible material. A tip is formed or applied at the distal end of the outer hollow tube to facilitate insertion of the catheter device into the uterus. The tip is most suitably made of a soft, pliant material which is readily deformable when it comes into contact with a resistive surface, such as the uterine wall or the fetus. Immediately behind the tip, toward the proximal end of the catheter, a plurality of small holes is formed through the wall of the outer hollow tube. The holes may be formed about the circumference of the outer hollow tube, and may also be positioned through the tip. The holes are sized to permit the passage of fluid therethrough, but are sufficiently small to prevent the movement of large particulates from the uterus therethrough. Alternatively, long narrow slits may be formed through the wall of the outer hollow tube extending from near the tip to a selected distance away from the tip. The outer tube is sealed at its proximal end to the housing.

The inner tube positioned within the outer hollow tube is also made of a flexible, biocompatible material. The inner tube is smaller in outer diameter than the outer hollow tube, such that a space or passage is formed between the inner wall of the outer hollow tube and the outer wall of the inner tube. The space becomes filled with fluid following insertion of the device within the uterus. The inner tube is sealed at its proximal end to the housing, to which the outer tube is also attached.

Proximate the distal end of the catheter and at the distal end of the inner tube is a pressure-compliant member which is deformable upon a change in pressure within the uterus. In the most preferred embodiment at present, the pressure-compliant member is a cylindrically-shaped balloon which is formed from a thin-walled, low durometer material, such as rubber or plastic, which is easily deformed within a given range of pressure variations. The balloon is closed at the distal end thereof and is attached at its proximal end to the open, distal end of the inner tube. As such, the inner tube and balloon define an internal closed air column which, in operation, is charged with sufficient air to maintain the balloon in a somewhat expanded state which is readily deformable in response to changes in intrauterine pressure. In a preferred embodiment, the balloon is attached to the inner tube with a flexible element, such as a resilient band, which expands to permit the escape of air from within the closed air column in the event that an excess of air pressure is present therein, thereby serving as a pressure relief valve.

The balloon is positioned within the outer hollow tube so that it extends from near the distal tip of the catheter to at least within several millimeters from the tip. The holes or slits formed in the outer hollow tube are distributed about the circumference of the outer hollow tube, and the pressure-complaint member, or balloon, is positioned in lateral proximity to the holes. When the pressure catheter is positioned within the uterus and is charged with sufficient air to inflate the balloon from a totally collapsed or flaccid state, fluid fills the space between the inner tube and outer tube and changes in fluid pressure within the uterus are manifested through the holes and in the fluid residing in the space. A collapsing deformation of the inflated balloon occurs with an increase in pressure, in turn leading to a detectable increase in pressure in the air column. An expanding deformation of the balloon occurs with a decrease in uterine pressure following a contraction and results in a detectable decrease in pressure in the air column. It is notable that the construction of the balloon and the material of its construction is such that no effect is experienced in the air column due to, for example, changes in temperature (i.e., the effects of Charles's Law), loss of gas due to permeability of the balloon material or water vapor absorption.

The inner tube may preferably be constructed with means for ameliorating any accumulation of condensation within the inner tube which may result from humidity in the atmosphere or from placement in the moist, warm environment of the uterus. In a preferred embodiment of the invention, a line of nylon or similarly hygroscopic material is positioned along the inner wall of the inner tube and extends from the proximal end of the inner tube to the distal end of the inner tube. The nylon line attracts moisture in the inner tube and distributes the moisture along the length of the inner tube so that any accumulation of condensation does not form in one area, such as near the distal end of the inner tube. The nylon line also adds structural reinforcement to the otherwise extremely collapsible inner tube and helps prevent complete closure of the inner tube in the event of kinking of the catheter.

The outer tube and the inner tube are both sealed to a housing which is configured as a connector for interconnecting with a reusable interface cable assembly. The outer hollow tube and inner tube are connected to the housing in a manner which provides a sealed space between the outer hollow tube and the inner tube extending to the holes or slits at the distal end of the outer tube. The housing is, most suitably, structured with an amino port which is in fluid communication with the space between the outer hollow tube and the inner tube. Thus, amniotic fluid can be withdrawn from the uterus through the holes formed in the distal end of the outer hollow tube and through the amino port. Further, fluid can be injected through the amino port and through the space between the outer hollow tube and the inner tube for delivery to the intrauterine environment, or to dislodge matter which may have temporarily occluded some of the holes formed in the outer hollow tube.

The connector of the housing is structured to closely accommodate the proximal end of the inner tube, the open end of which is positioned at the proximal extremity of the connector. An O-ring or other annular seal may, in one embodiment, be positioned about the exterior of the connector in proximity to the proximal end of the inner tube, although the inner tube may be foreshortened and a passage in the housing might extend to the proximal end thereof, the O-ring extending about the passage. The connector of the housing is sized to interconnect with a connector formed as a mating part of a coupling positioned at the distal end of the reusable interface cable assembly. In one embodiment of the invention, the connector of the reusable interface cable assembly may be structured as a female connector having a cavity which is sized to snugly receive a male connector structured as part of the housing. The female connector is structured with a selected volume which contains enough air to charge the air column, or inner tube and balloon, upon engagement of the male and female connectors. That is, as the male connector is longitudinally inserted into the female connector cavity, a small volume of air occupying a portion of the female connector means is trapped and is automatically forced into the air column during connection to at least partially inflate the balloon. The male connector, having an external O-ring, acts as a piston or plunger along the travel of the male connector into the cavity, the O-ring establishing an air-tight seal between the male and female connector elements to trap, pressurize and maintain an appropriate amount of air in the air column. In an alternative embodiment, the housing to which the outer hollow tube and inner tube are connected may be formed as a female connector having a cavity sized to receive a male connector structured at the distal end of the reusable interface cable.

A coupling formed at the distal end of the reusable interface cable assembly may preferably house a pressure detection device, such as a pressure transducer. In the presently preferred embodiment, the coupling houses a pressure transducer having a diaphragm which is positioned in close proximity to the open proximal end of the inner tube when the male connector means is fully inserted into the female connector and the air column is charged. Thus, as pressure within the uterus increases, an increase in fluid pressure brought about by an increase in fluid pressure across the holes or slits in the outer hollow tube applies sufficient pressure to the balloon to deform (i.e., partially collapsed) the balloon slightly. The change in pressure exerted on the air column with deformation of the balloon is translated through the air column to the diaphragm of the pressure transducer, and the change in pressure is detected by the pressure transducer. The transducer is in electrical communication, via the reusable interface cable of the assembly, with a fetal monitor which provides a reading of the pressure change.

In operation, the intrauterine pressure catheter of the present invention is inserted through the vagina and into the uterus by known techniques of intrauterine pressure catheter placement. A removable introducer sheath may be initially positioned about the outer tube of the catheter to assist in placement of the IUP catheter. Once the IUP catheter is positioned, the introducer sheath is drawn rearwardly toward the proximal end of the outer tube. The housing of the catheter may be formed with a protrusion against which the introducer sheath may be contacted to initiate a slit in the sheath. The sheath is then removed from about the outer tube and is discarded. Upon initial insertion into the uterus, the pressure-compliant member, or balloon, is substantially empty (i.e., not filled with air). The male connector of the housing, in a first embodiment, is inserted into the female connector cavity of the coupling of the reusable interface cable assembly. With insertion of the male connector into the female connector of the reusable interface cable assembly, the air column becomes charged, or filled with air. The pressure-compliant member is, as a result, at least partially filled with air and the membrane of the pressure-compliant member is primed for pressure sensing. The electrical connector at the proximal end of the reusable interface cable assembly is then plugged into the fetal monitor and the monitor is powered on. The proximal end of the IUP catheter may conveniently be taped to the thigh of the patient to keep the catheter in place.

The IUP of the present invention is configured so that the patient may move without compromising the calibration or placement of the catheter. The present invention, therefore, provides a particular advantage over known devices since the sensor device of the present invention can be reset, or "zeroed", at any time if the patient's movements should compromise the charge in the air column. The device can even be reset while positioned in the uterus, which is not typically possible with known devices. In one embodiment of the present invention, the patient may be attached to the fetal monitor by the reusable interface cable and is, therefore, restricted in mobility. In an alternative embodiment, a wireless telemetry unit may be used which includes a reusable transmitter unit having a connector and an associated pressure detection device, as previously described, which is attachable to the connector of the housing and a reusable remote receiver which is attached to the fetal monitor. Intrauterine pressure changes may then be monitored on a constant basis even while the patient is ambulatory, the pressure detection data being sent to the fetal monitor through the telemetry unit.

BRIEF DESCRIPTION OF THE DRAWINGS

In the drawings, which illustrate what is presently considered to be the best mode for carrying out the invention.

DETAILED DESCRIPTION OF THE PREFERRED EMBODIMENT

Figures 1, 2, 3, 4, 9:
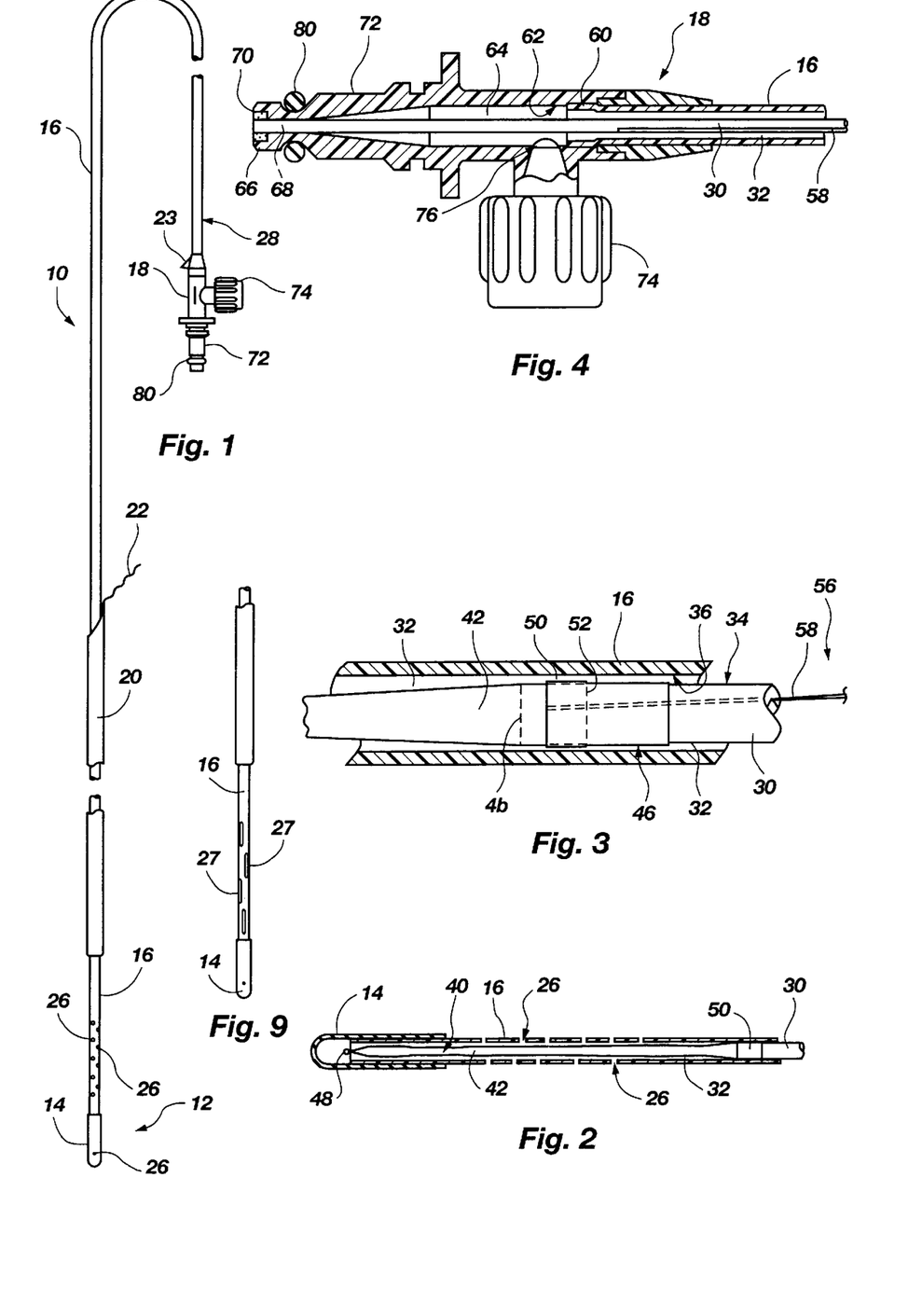
FIG. 1 is a view in elevation of the intrauterine pressure catheter of the present invention.
FIG. 2 is an enlarged view in longitudinal cross section of the tip of the intrauterine pressure catheter shown in FIG. 1.
FIG. 3 is an enlarged view in cutaway longitudinal section of the attachment of the pressure-compliant member of the catheter to the inner tube.
FIG. 4 is an enlarged partial longitudinal cross section of the proximal end of the intrauterine pressure catheter showing the housing illustrated in FIG. 1.
FIG. 9 is an enlarged view in elevation of the distal end of the catheter of an alternative embodiment.
Figure 7:
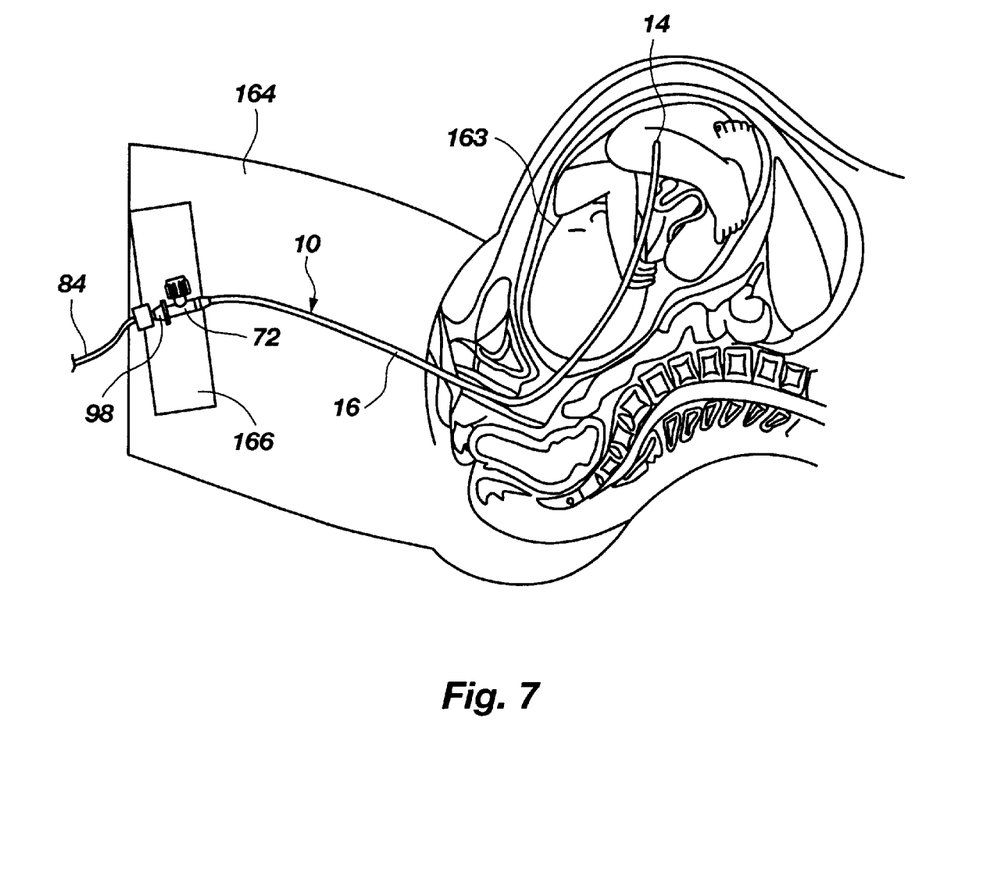
FIG. 7 is a view in partial anatomical cutaway illustrating the insertion of the intrauterine pressure catheter within the uterus of a patient and the attachment of the housing to the patient's leg.

FIG. 1 illustrates the disposable intrauterine pressure (IUP) catheter 10 of the present invention. At the distal end 12 of the catheter 10 there is formed a soft, pliant tip 14 which facilitates insertion of the IUP catheter 10 into the uterus. The soft tip 14 may preferably be formed of a material which is pliant enough to deflect or give as the tip 14 encounters a resistive force, such as the fetus, placenta or the uterine wall. A low durometer plastic or elastomer such as polyvinyl chloride (PVC) or a polyurethane is highly suitable. The tip 14 is attached to an elongated outer hollow tube 16 which extends from the tip 14 at its distal end to a housing 18 at its proximal end. The outer hollow tube 16 is formed of flexible, biocompatible material such as PVC or a polyolefin, with sufficient wall thickness to resist collapse under normal conditions, and sized in length to extend from within the uterus of a patient to outside the body of the patient, as illustrated in FIG. 7. Thus, for example, the outer hollow tube may range in length from 60 cm to 90 cm. A tear-away sheath 20 may be initially positioned about the outer hollow tube 16 to facilitate insertion of the IUP catheter 10 into the uterus. After insertion of the IUP catheter 10, the tear-away sheath 20 is removed, such as by pulling on thumb tab 22 and slitting against a ramp or other protrusion 23 on the proximal end of catheter 10.

A plurality of holes 26 is formed through the wall of the outer hollow tube 16 immediately behind the tip 14. The pattern of holes 26 may vary, but, preferably, the holes 26 are distributed about the circumference of the outer hollow tube 16 and longitudinally therealong to allow fluid to enter into the outer hollow tube 16 from any direction thereabout. A plurality of holes 26 is provided so that, if any one or more holes 26 should become clogged with matter from the amniotic fluid, other holes 26 will be available for allowing passage of fluid, and transmission of fluid pressure, therethrough. The holes 26 extend for a distance beyond the tip 14 in the direction of the proximal end 60 of the outer hollow tube 16. The holes 26 may extend anywhere from one millimeter to several centimeters beyond the tip 14. One or more holes 26 may also be formed through the tip 14. In an alternative embodiment, slits 27 may be formed through the wall of the outer hollow tube 16 as shown in FIG. 9. It is preferable that the holes or slits extend proximally of the most proximal end of a balloon 42 (see below) disposed within tube 16 so that excessive infusion of fluid entering tube 16 will not disturb the balloon and induce artifact into the pressure signal generated thereby.

An inner tube 30 is disposed within the outer hollow tube 16, as shown more fully in FIGS. 2–4. The inner tube 30 extends from a housing 18, to which it is sealed, to near the distal end 12 of the IUP catheter 10. The inner tube 30 is hollow and is made of flexible, biocompatible material, such as polyurethane. The inner tube 30 is sized in diameter to fit within the outer hollow tube 16 and to leave a space or passage 32 between the outer wall 34 of the inner tube 30 and the inner wall 36 of the outer hollow tube 16, as best shown in FIG. 3. Inner tube 30 is preferably a "bump" tube, of increasing O.D. toward the distal end thereof. The space 32 becomes filled with fluid following insertion of the IUP catheter 10 into the uterus.

A pressure-compliant member 40 is associated with the inner tube 30 and is positioned within the relatively non-compliant outer hollow tube 16 for protection against direct extreme pressure conditions exerted by surfaces (i.e., the uterine wall or fetus) or objects within the intrauterine environment. The pressure-compliant member 40, which is air-filled, as will be described below, is structured to deflect or deform upon an increase in pressure within the uterus, and to expand again upon a subsequent decrease in pressure. Therefore, a particularly suitable pressure-compliant member 40 may be a balloon 42 formed of a thin-walled, flexible, low durometer material such as C-Flex® elastomer, which is relatively easily deformed with a small increase in pressure. As shown in FIG. 2, the balloon 42 may be formed as an elongated, cylindrical body which is disposed about and attached to the open, distal end 46 (FIG.3) of the inner tube 30 and which is heat-sealed at the opposing end 48 of the balloon 42. The balloon 42 may be positioned within the outer hollow tube 16 to extend from the distal end 46 of the inner tube 30 to near the extremity of the tip 14. The balloon 42 may generally have an outer diameter (o.d.) approximately equal to the o.d. of the inner tube 30 such that a space 32 is formed between the balloon 42 and the inner wall 36 of the outer hollow tube 16.

Air occupies the interior of the inner tube 30 and is at atmospheric pressure prior to use of the IUP catheter. The inner tube 30 and the balloon 42 attached to the inner tube 30 may, therefore, form or define an air column which extends from the housing 18 to near the tip 14 of the IUP catheter 10. When the IUP catheter 10 is attached to an interface cable, as explained further below, the air column becomes filled, or "charged", with an additional quantity of air. The additional air charged into the air column fills the balloon 42, at least partially, to a selected volume. The material of the balloon 42 is very pliant due to its thin wall and the low durometer material used in its construction, and the balloon 42 deforms easily, and substantially without artifact introduced by the material of the balloon itself, with a given change in pressure external to the balloon 42. The material of the balloon may, for example, be about a 30 A Shore durometer hardness. A particularly suitable material for use in forming the inner tube 30 may be C-Flex® synthetic elastomer (Consolidated Polymer Technologies, Inc., Largo, Fla.) of 0.001–0.002 in. (1–2 mil) wall thickness, or any other similar material having similar durability and flexibility. Regardless of the material employed, less than 5 mm Hg of external pressure maximum should be required to collapse balloon 42 when its interior is vented to atmospheric pressure. The uterus typically has a 5–30 mm Hg resting tone, and therefore will ensure collapse of balloon 42 upon insertion of catheter 10 and before charging. The collapse of balloon 42 before charging the air column, as subsequently described, provides an accurate pressure signal.

The balloon 42 may be attached to the distal end 46 of the inner tube 30 in any appropriate manner. However, as illustrated in FIG. 3, the balloon 42 may preferably be attached to the inner tube 30 by a resilient, elastomeric band 50 which surrounds the circumference of the proximal end 52 of the balloon 42 which is positioned over the distal end 46 of the inner tube 30. The resilient band 50 is sufficiently strong to maintain the proximal end 52 of the balloon 42 on the inner tube 30, but is sufficiently resilient to release any excess air pressure above a predetermined threshold pressure. It should be understood that too high an internal air column pressure will reduce the sensitivity of the device for measuring pressure changes and will increase the susceptibility of the pressure monitoring to temperature-induced artifacts. Balloon 42 may burst due to its relatively fragile construction if over pressurized.

The balloon 42 is positioned within the outer hollow tube 16 to be substantially laterally aligned with the holes 26, or slits 27, which are formed through the outer hollow tube 16. In an exemplary embodiment, the balloon is about 5 centimeters long, while the holes are placed over a 7–8 centimeter range from the tip 14, thus allowing fluid to bypass the balloon as previously mentioned. The extended hole pattern also addresses short occlusion areas due to contact by the uterus. Thus, when the IUP catheter 10 is positioned within the uterus, fluid fills the space 32 formed between the outer hollow tube 16 and the inner tube 30, thereby substantially surrounding the balloon 42 with fluid and providing a lubricating effect to alleviate sticking of the balloon 42 to the inner wall 36 of the outer tube 16. Very small matter from the amniotic fluid may also enter through the holes 26 and occupy the space 32. To avoid any sticking of the inner tube 30 to inner wall 36 of the outer hollow tube 16, brought about by the existence of matter in the space 32, the exteriors of inner tube 30 and balloon 42 may be coated during manufacturing with a surfactant which, upon wetting, provides a slippery coating which prevents the inner tube 30 from sticking to the inner wall 36. One example of a suitable surfactant is sodium lauryl sulfate. The inner tube 30 and balloon 42 may also be exterior-coated with an anticoagulant to prevent clotting of blood cells in the space 32 and about the inner tube 30.

The air column formed in the inner tube 30 and balloon 42 may have an amount of condensation associated therewith as a result of ambient humidity or minute amounts of water permeating through the balloon 42 or through the inner tube 30 after the IUP catheter 10 has been positioned in the uterus (which averages a temperature of about 37° C.) for a period of time. To avoid an accumulation of condensation in the air column, therefore, the inner tube 30 may be structured with a moisture-collecting element 56 to draw or collect moisture within the tube 30. As shown in FIG. 3, the moisture-collecting element 56 may suitably be a line or strand 58 of hygroscopic material, such as nylon, which collects condensate and wicks and distributes the moisture along the length of the line 58. The absorbent line 58 may preferably extend from the distal end 46 of the inner tube 30 to near the proximal end 28 of the catheter 10. The line may be, for example, approximately 0.01 inch (10 mil) in diameter, and is anchored to the interior wall of inner tube 30 by application of a drop of adhesive applied at the distal end of the tube, the line material drawing the adhesive along the line into the tube. The other end of line 58 is free, but the line is rigid enough to maintain itself in place with one anchor point. The absorbent line 58 also provides a degree of structural support against collapse to the inner tube 30, which helps prevent the otherwise flexible inner tube 30 from kinking and compromising the air column, and prevents total closure of inner tube 30 upon kinking.

As shown in FIG. 4, both the outer hollow tube 16 and the inner tube 30 are attached to the housing 18 in sealing engagement therewith. The proximal end 60 of the outer hollow tube 16 is attached to the inner surface 62 of the housing 18. The inner tube 30, which extends through the outer hollow tube 16, enters through the interior lumen 64 of the housing 18 and extends to the proximal extremity 66 of the housing 18. The proximal end 68 of the inner tube 30 is sealed to the proximal extremity 66 of the housing 18 by any suitable means, such as by a sealing gasket and/or adhesive 70. The proximal end 68 of the inner tube 30 remains open.

In the embodiment of the device illustrated in FIGS. 4 and 6, the housing 18 is structured with a male connector 72 which is sized to be inserted into a female connector of a reusable interface cable assembly as described more fully hereinafter. The male connector means 72 of the IUP catheter 10 includes an O-ring or other annular seal element 80 which facilitates an air-tight seal between the IUP catheter 10 and the reusable interface cable assembly (FIG. 5).

The housing 18 may also be formed with an amino port 74 having an opening 76 which communicates with the interior lumen 64 of the housing 18. The interior lumen 64 is contiguous with the space 32 formed between the inner tube 30 and the outer hollow tube 16. Therefore, fluid entering the space 32 from the amniotic environment may be sampled or withdrawn from the amino port 74. Alternatively, fluid may be injected into the uterine environment through the amino port 74. In particular, a bolus of fluid can be injected into the amino port 74 to flush the holes 26 formed near the tip 14 of the IUP catheter 10, thereby dislodging any matter which may be occluding the holes 26.

Figures 5, 6:
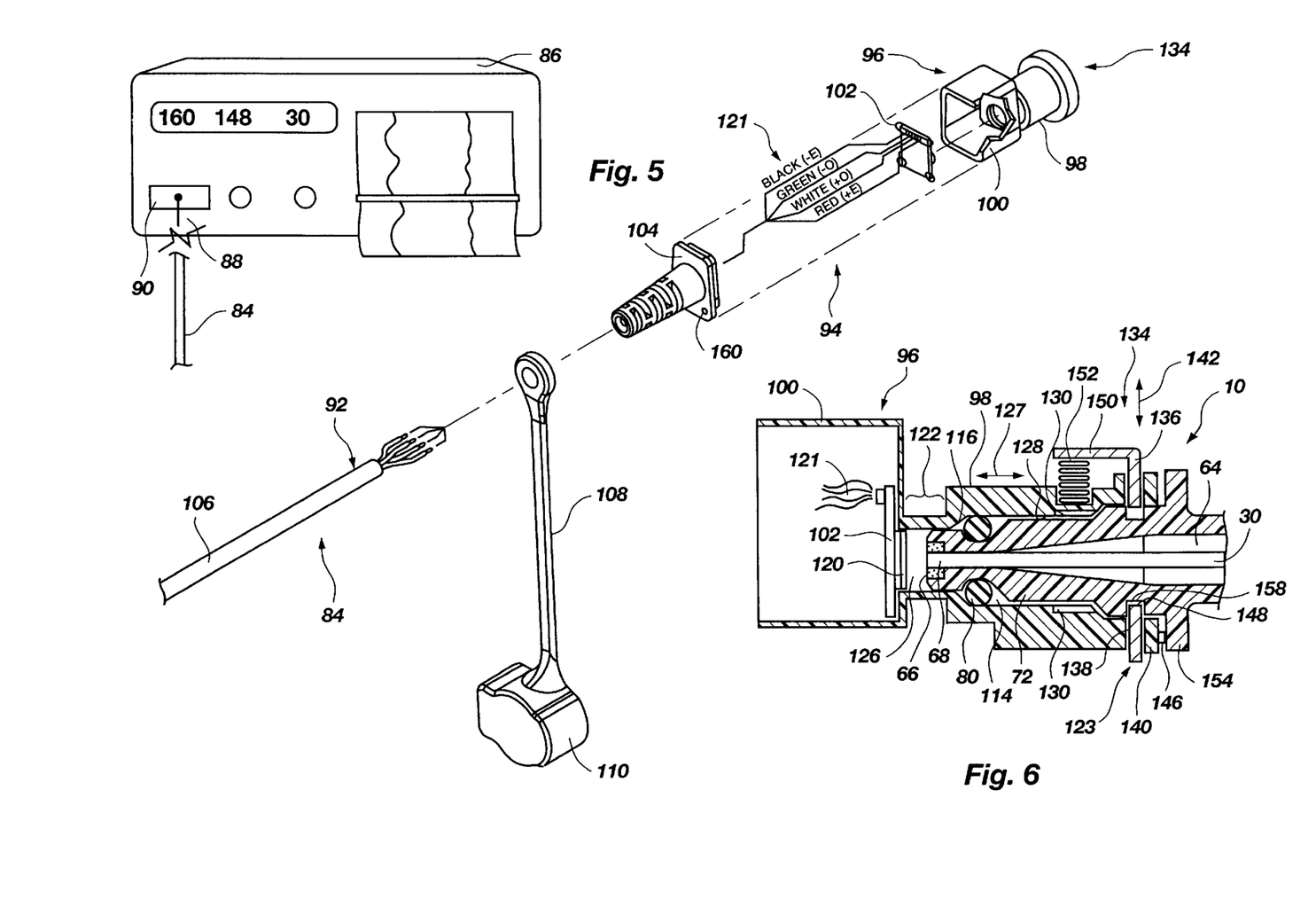
FIG. 5 is an exploded view of the end of the reusable interface cable assembly with the female connector and housing the pressure detection device, the cable of the assembly extending as shown to a monitor.
FIG. 6 is an enlarged view in longitudinal cross section illustrating the male connector of the housing inserted in the female connector of the reusable interface cable assembly.
Figure 5:
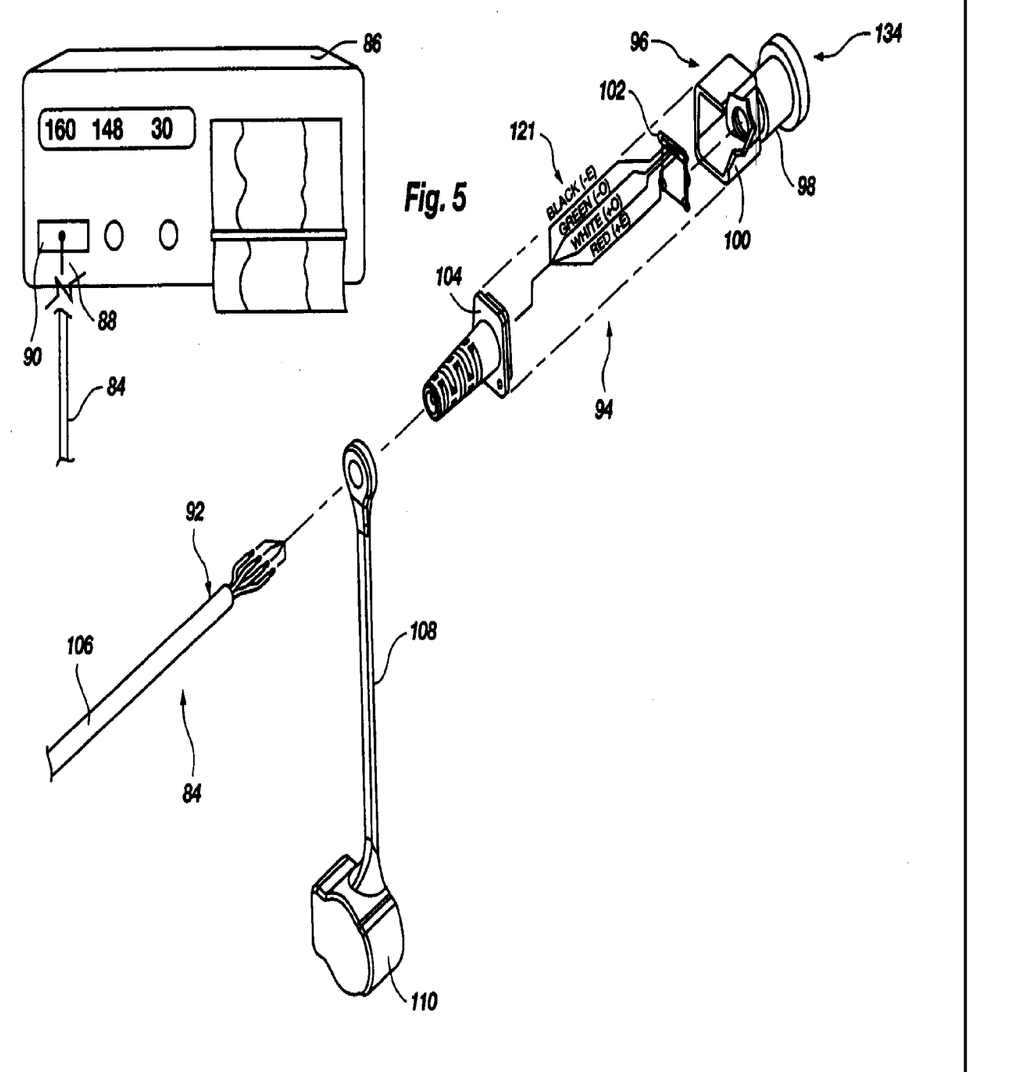

The IUP catheter 10 as thus far described is detachably attached to a reusable interface cable assembly 84 which is structured to be plugged into a fetal monitor 86, as illustrated in FIG. 5. The reusable interface cable assembly 84 has, at its proximal end 88, an electrical connector 90 which is sized and configured for attachment to a fetal monitor 86. At the distal end 92 of the reusable interface cable assembly 84 is a pressure detection device 94 which interfaces with the air column of the IUP catheter 10 to detect changes in intrauterine pressure. The pressure detection device 94 may, as shown in FIGS. 5 and 6, comprise a coupling 96 structured with a female connector 98 sized to receive the male connector 72 of the IUP catheter 10, an enclosure 100 for retaining a pressure sensor 102 and an end cap 104 for capping the enclosure 100 and attaching the pressure detection device 94 to a tubular cable 106 of the reusable interface cable assembly 84. A protective cover 108 may also be provided on the reusable interface cable assembly 84 and have a cap 110 sized to fit over the exposed end of the female connector 98 when the reusable interface cable assembly 84 is not connected to the IUP catheter 10.

As shown more clearly in FIG. 6, the female connector 98 is attached to, or integrally formed, with the enclosure 100. The female connector 98 has an internal bore or cavity 114 which is sized in internal diameter and length to snugly receive the male connector 72 of the IUP catheter 10. Upon insertion of the male connector 72 in the bore 114 of the female connector 98, the O-ring 80 becomes seated against an inner wall 128 of the internal bore 114 to form an air-tight fit. Further, the proximal extremity 66 of the housing 18 and the open proximal end 68 of the inner tube 30 are positioned in close proximity to the pressure sensor 102 retained within the enclosure 100, minimizing dead space in the system. The pressure sensor 102 may, most suitably, be a pressure transducer, such as an NPC-109 manufactured by Lucas NovaSensors of Fremont, Calif., having a deformable diaphragm 120 which is positioned toward the female connector means 98. Wiring 121 extends from the pressure sensor 102, through the enclosure 100 and to the proximal end 88 of the cable 106 for communication to monitor 86.

The bore 114 and throat 122 lying between the mouth 123 of the female connector 98 and the enclosure 100 of the coupling 96 define an internal space 126 which contains a predetermined or selected volume of air prior to insertion of the male connector 72 into the bore 114 of female connector 98. Thus, as the male connector means 72 is inserted like a piston or plunger into the bore 114 of female connector 98 in the direction of arrow 127, part of the volume of air contained within the internal space 126 of the bore 114 is displaced by male connector 72. The displaced volume of air is sufficient to "charge" or fill the balloon 42 with an appropriate amount of air to expand the balloon 42 to function with desired sensitivity responsive to a given range of pressure values, as described further below. As the male connector means 72 is inserted into the female connector means 98 and the O-ring 80 registers against the inner wall 128 surrounding the internal bore 114, excess air is released from the internal bore 114 through indented flutes 130 formed in the inner wall 128 so that the precharge volume of air is precisely defined. Stated another way, the effective air volume trapped in the air column is defined by the inward stroke or travel of male connector 72 from the point at which O-ring 80 passes flutes 130 until male connector 72 is fully inserted in female connector 98.

The female connector 98 of the coupling 96 may be structured with a locking device 134 for retaining the male connector 72 in exact position within the female connector 98. As shown in FIG. 6, an exemplary locking device 134 may comprise a slidable ring 136 which is positioned against, and slides within, a groove 138 formed in the outer flange 140 of the female connector 98. The slidable ring 136 moves in the direction of arrow 142. A detent 146 engages a lip 148 of the slidable ring 136 when the locking means 134 is in an unlocked position and thumb tab 150 is depressed against spring 152. As the male connector means 72 is inserted into the female connector means 98, an outwardly extending flange 154 of male connector means 72 depresses the detent 146, thereby disengaging the slidable ring 136 from its engagement with the detent 146, and the spring 152, pushing against the thumb tab 150, moves the slidable ring 136 laterally. The lip 148 of the slidable ring 136 is urged into a groove 158 formed in the male connector means 72 and locks the male connector means 72 in place. The male connector means 72 can only be released from the female connector means 98 by depressing the thumb tab 150 and engaging the detent 146 with the lip 148 once again.

Upon insertion of the IUP catheter 10 into the uterus, fluid fills the space 32 between the outer hollow tube 16 and the inner tube 30, and the balloon is in a substantially deflated stated. With charging, the balloon 42 becomes at least partially filled with air. Thus, depending on how much air is in the balloon 42 prior to charging, the balloon 42 may be anywhere from 40% to 70% filled to capacity with air following charging. The volume of air which respectively fills the inner tube 30 and balloon 42 will vary, of course, with the size and length of the inner tube 30 and balloon 42. However, the volume of air in the air column is such that at least fifty percent of the air volume will remain in the balloon 42 with a 100 mm Hg increase in pressure. In prototype designs, for example, it was found that about a 200 microliter volume balloon, charged with about 100 microliters of air, provides satisfactory signals when an external pressure of 100 mm Hg is applied. It is desirable not to overfill balloon 42 and thereby introduce the structure of the balloon into the signal. In other words, the flaccidity of the partially-filled working volume of balloon 42 will prevent the occurrence of aberrant effects in pressure detection due to temperature changes as dictated by Charles's Law, or aberrant effects which might be introduced signal artifacts due to the balloon wall internal forces.

The low durometer material of the balloon 42 allows the surface of the balloon 42 to deform with an increase in pressure. Therefore, an increase in intrauterine pressure generally greater than about 1 mm Hg will deform the balloon 42 and, in turn, modify the pressure in the air column within the balloon 42 and inner tube 30. The change in pressure is translated down the air column to the diaphragm 120 of the pressure sensor 102. Deflection of the diaphragm 120 resulting from an increase in pressure is converted to an electrical signal by the transducer and is relayed to the fetal monitor 86 through the cable 106. Similarly, a subsequent decrease in intrauterine pressure is also relayed by subsequent expansion of the balloon 42. Maximum uterine pressure will not fully collapse balloon 42 when the air column is charged.

It should be noted that "zeroing" is simplified with the present invention because atmospheric pressure exists on both sides of the diaphragm 120 prior to insertion of the male connector 72 into the female connector 98 because the internal bore 114 is exposed to atmosphere and the enclosure 100 behind diaphragm 120 is also exposed to atmosphere by virtue of an aperture 160 (FIG. 5) formed through the end cap 104 of the enclosure 100. Therefore, "true zero" exists prior to plugging the IUP catheter 10 into the reusable interface cable assembly 84, and "true zero," or zero differential across the membrane, can be attained at any time by simply disconnecting the catheter from the reusable connector, even when the catheter remains in the uterus. The simplicity of "zeroing" the device on an initial or continuing basis provides a significant advantage over prior art systems. It may be noted that some suitable materials which may be used in manufacturing the balloon 42 may be permeable to air and water such that, over time, air may dissipate from the balloon 42. However, the materials from which the balloon may be made are of sufficiently low permeability that the balloon 42 will remain appropriately charged for two to three hours. Even if pressure within the air column should drop below the normative value during use, the IUP catheter can be simply and quickly "re-charged" by disconnecting the male connector means 72 from the female connector means 98 and plugging it back in. The air column can thus be re-charged as often as necessary.

Catheter 10 is preferably packaged in a gamma-ray sterilized package, and is disposable after use. Interface cable assembly 84 is separately supplied, and may vary in electrical output characteristics depending upon the fetal monitor with which it is to be associated. Stated another way, the electronics of assembly 84 may be varied as known in the art to provide an appropriate output signal from sensor 102 to monitor 86, which may comprise any commercially-available monitor, including, by way of example only, the Hewlett-Packard Model 8040 and the Corometrics 115. The manufacturer and model number of the monitor is of no significance to the invention.

Figure 10:
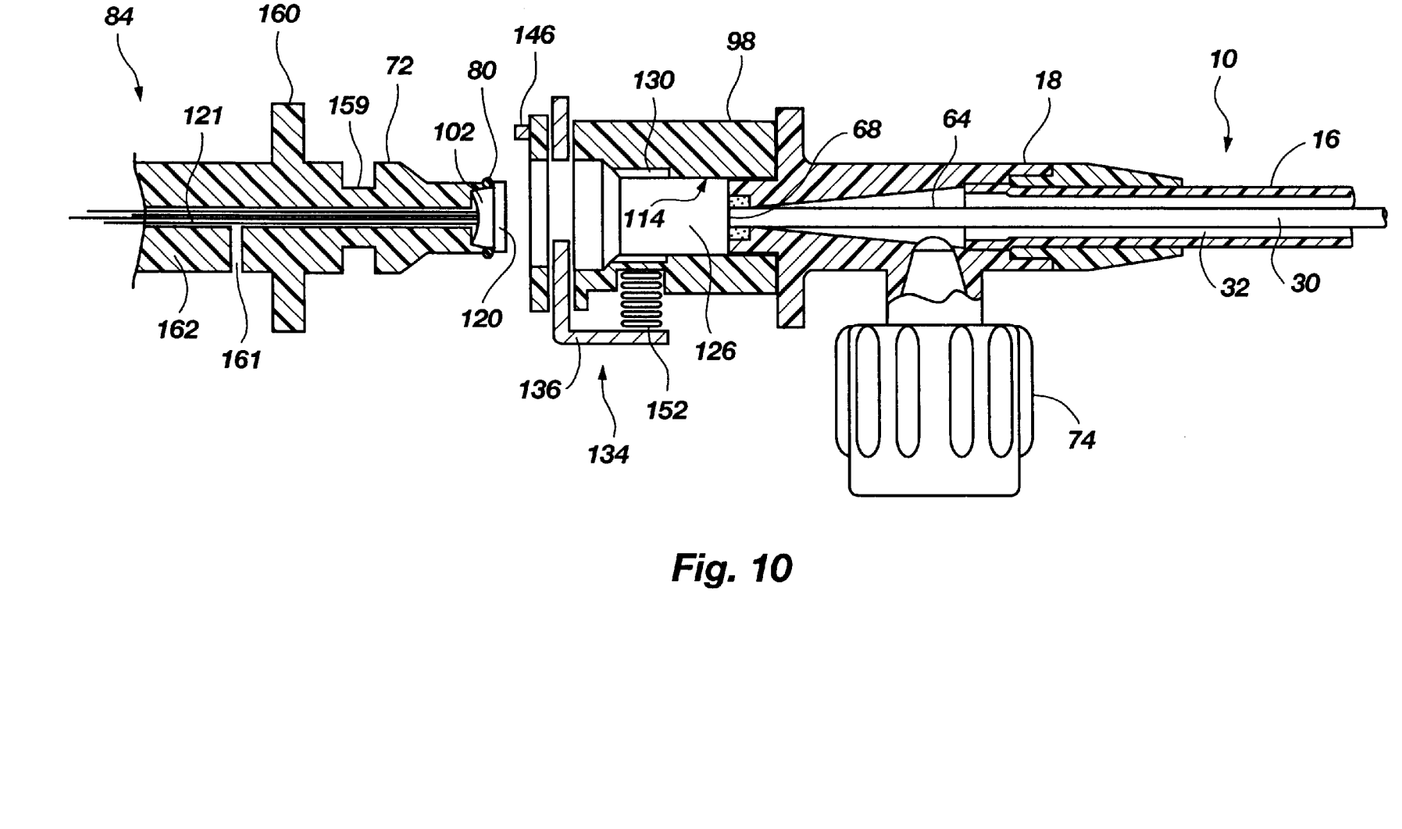
FIG. 10 is a view in cross section of an alternative embodiment of the invention where the connectors are differently structured.

In an alternative embodiment to that previously described, the housing 18 of the IUP catheter 10 may be formed as a female connector 98, as illustrated in FIG. 10 where like structures are shown with like reference numerals. Thus, the female connector 98 of the housing 18 may be formed with a bore 114 having an internal space 126 which is sized to receive the male connector means 72 formed at the distal end of the reusable interface cable assembly 84. The pressure sensor 102 may be positioned at the distal extremity of the reusable interface cable with the diaphragm 120 oriented toward the open proximal end 68 of the inner tube 30 upon insertion. Thus, as the male connector 72 of the reusable interface cable assembly 84 is inserted into the bore 114 of the female connector 98 of the housing 18 in the manner or a piston or plunger, the volume of air occupying the internal space 126 is displaced by the male connector 72. The displaced volume of air charges the air column, thereby partially inflating the balloon 42 with air, and excess air may be released from the internal space 126 as the O-ring associated with the male connector 72 contacts the wall of the bore 114 and forms an air-tight seal therewith. As previously described, the female connector 98 may be structured with locking means 134 comprising a slidable ring 136 which engages a groove 159 formed in the circumference of the male connector 72. A flange 160 formed about the circumference of the male connector 72 impacts against the detent 146 to engage the locking means 134 as previously described. An aperture 161 is also formed through the wall 162 of the reusable interface cable assembly 84 to maintain ambient air pressure on the inner surface of the diaphragm 120.

FIG. 7 illustrates how the IUP catheter 10 of the present invention may be inserted into the intrauterine space 163 during labor to monitor changes in pressure. The IUP catheter 10 is inserted, using known techniques, by passing the tip 14 through the vagina and advancing the outer hollow tube 16 until the IUP catheter is inserted between thirty and forty-five centimeters, as measured from the tip 14. The removable sheath 20 is withdrawn from the distal end of the IUP catheter 10 and is removed from about the catheter 10. The male connector means 72 of the IUP catheter 10 is then inserted into the female connector means 98 of the reusable interface cable assembly 84 to charge the air column and the reusable interface cable assembly 84 is plugged into the fetal monitor 86 (FIG. 5). The IUP catheter 10 may then be secured to the leg 164 of the patient by appropriate means, such as a piece of tape 166.

Figure 8:
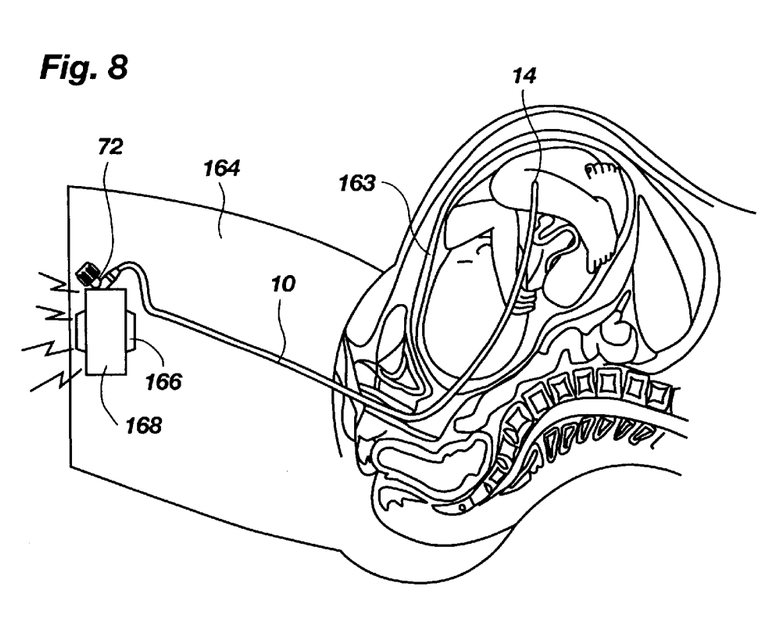
FIG. 8 is a view in partial cutaway illustrating an alternative means of monitoring intrauterine pressure changes using the invention via wireless telemetry.

The configuration illustrated in FIG. 7 allows the patient a certain amount of movement during the labor process, but essentially tethers the patient to the fetal monitor 86. Therefore, an alternative means of monitoring pressure data is illustrated in FIG. 8 where the male connector 72 of the IUP catheter 10 is attached to a female connector 98 as previously described (not shown in FIG. 8), the female connector means being mechanically attached to and electrically communicating with the transmitter 168, the transmitter 168 also housing the pressure sensor 102 (not shown in FIG. 8). Transmitter 168 transmits signal data corresponding to the detected changes in intrauterine pressure to a receiver 170 associated with a fetal monitor 86. The telemetry system as described preferably employs electromagnetic signals, and preferably low radio frequency signals, over a range of up to about forty feet. In this embodiment, the patient has greater mobility in moving around during labor.

The pressure catheter of the present invention provides significant improvements over prior intrauterine pressure catheter devices because it is simply constructed, is easy to use, is constructed for safe and comfortable insertion and simplifies zeroing, thereby avoiding constant recalibration. Moreover, the closed air column provides for isolation of the gas pressure-transfer medium from bodily fluids and fluids injected into the body of the patient. Thus, the pressure catheter of the present invention is suitable for detecting pressure changes in a number of medical procedures, including fetal monitoring during labor, intracranial pressure monitoring and arterial or venous pressure monitoring. Hence, reference herein to specific details of the illustrated embodiments is by way of example and not by way of limitation. It will be apparent to those skilled in the art that many additions, deletions and modifications to the illustrated embodiments of the invention may be made without departing from the spirit and scope of the invention as defined by the following claims. For example, the balloon may be widened and shortened to optimize volume and increase sensitivity, and disposed in an enlarged portion of the outer tube, or even a molded "cage" between the distal end of the outer tube and the catheter tip. Simpler connectors may be used between the catheter and the cable assembly and a plunger-type charging mechanism incorporated in the cable-end connector.

What is claimed is:

1. A pressure catheter for detecting changes in pressure within a patient's body, comprising:

an elongated outer hollow tube defining a fluid channel extending longitudinally through an interior thereof, and at least one aperture formed in said outer hollow tube to provide communication between an exterior of said outer hollow tube and said fluid channel;

an inner tube positioned at least partially within said elongated outer hollow tube;

a flaccid, pressure-compliant member defining an interior chamber in communication with said inner tube, said flaccid, pressure-compliant member having an exterior surface exposed by structure of said catheter to a fluid environment within said patient's body when inserted therein and substantially protected by structure of said pressure catheter from direct contact with tissues within said patient's body while inserted therein; and a charging structure for charging air into said inner tube, said inner tube and said flaccid, pressure-compliant member defining a closed air column operative to transmit said changes in pressure acting upon said flacid, pressure-compliant member through said inner tube subsequent to receiving a charge of air.

2. The pressure catheter of claim 1, wherein said pressure-comdliant member comprises a thin-walled balloon formed of flexible material.

3. The flaccid, pressure catheter of claim 2, wherein said charging structure includes a housing to which at least said inner tube is secured in sealing engagement therewith.

4. The pressure catheter of claim 3, further comprising a pressure detection device positioned in communication with said inner tube to detect a pressure change in said closed air column resulting from a deformation of said balloon.

5. The pressure catheter of claim 1, further comprising a moisture-collecting element disposed within said inner tube.

6. The pressure catheter of claim 3, wherein said housing is secured in sealing engagement with said outer hollow tube and includes a port in fluid communication with said fluid channel and extending to the exterior of said housing.

7. The pressure catheter of claim 1, further comprising a soft, pliant tip formed on an end of said elongated outer hollow tube for insertion within a body.

8. A pressure catheter for detecting changes in pressure within a patient's body, comprising:

an elongated hollow tube having a first end and a second end;

a channel extending longitudinally through said elongated hollow tube from proximate said first end to proximate said second end of said elongated hollow tube, said channel being in sealed communication with an interior chamber of a pressure-compliant member disposed proximate said second end of said elongated hollow tube, said catheter including structure for exposing an exterior surface of said pressure-compliant member to a fluid environment within said patient's body when said second end of said elongated hollow tube is inserted therein and protecting said pressure-compliant member from direct contact with tissues of said patient's body while inserted therein;

a charging structure associated with an outlet of said channel proximate said first end of said elongated hollow tube for charging a volume of air into, and sealing said volume of air within, said channel and said interior chamber of said pressure-compliant member;

a pressure detection device operable to detect pressure changes in said sealed volume of air; and an electronic signaling structure for transmitting detected pressure data to a monitor.

9. The apparatus of claim 8, wherein said pressure-compliant member comprises a thin-walled balloon of flexible material.

10. The apparatus of claim 9, wherein said balloon is sealingy secured in communication with said channel by a resilient structure surrounding a portion of said balloon into which extends a structural projection of said catheter into said balloon defining an end of said channel.

11. The apparatus of claim 8, further comprising a moisture-collecting element within said channel.

12. The apparatus of claim 11, wherein said moisture-collecting element comprises an elongated line of hygroscopic material positioned within said channel.

13. The apparatus of claim 12, wherein said hygroscopic material comprises nylon.

14. The apparatus of claim 8, further comprising a housing secured to said elongated hollow tube proximate said first end and including a first connector, and wherein said pressure detection device is associated with a second connector configured to interconnect with said first connector in air-tight registration therewith, said first and second connectors comprising said charging structure.

15. The apparatus of claim 14, wherein said pressure detection device includes a pressure transducer having a diaphragm positioned for exposure to said volume of air.

16. The apparatus of claim 14, further including a locking device for retaining said first connector in air-tight registration with said second connector.

17. The apparatus of claim 14, wherein said elongated hollow tube defines a fluid channel extending from proximate said second end of said elongated hollow tube to said housing, and said housing includes a port in communication with said fluid channel, said port extending to an exterior of said housing.

* * * * *

UNITED STATES PATENT AND TRADEMARK OFFICE
CERTIFICATE OF CORRECTION

PATENT NO. : 5,984,879
DATED : November 16, 1999
INVENTOR(S) : W. Dean Wallace, Christopher A. Cutler and Steven R. Smith It is certified that error appears in the above-identified patent and that said Letters Patent is hereby corrected as shown below:

Drawings,
Figure 5, delete reference numeral "160" and associated lead line as shown on attached page.

Column 8,
Line 30, change "catheter · 10" to -- catheter 10 --.

Column 12,
Line 18, change "aperture 160" to -- aperture --.

Column 14,
Line 32, after "said" and before "pressure" insert -- flaccid --.
Line 33, change "comdliant" to -- compliant --.
Line 35, after "The" and before "pressure" delete "flaccid".

Signed and Sealed this

Thirteenth Day of June, 2006

JON W. DUDAS
*Director of the United States Patent and Trademark Office*